United States Patent [19]

Meller

[11] Patent Number: 5,334,013
[45] Date of Patent: Aug. 2, 1994

[54] HIGH SPEED DENTAL DRILL WITH POSITIVE PRESSURE AIR DRIVE

[76] Inventor: Moshe Meller, 448 Sayre Dr., Princeton, N.J. 08540

[21] Appl. No.: 2,350

[22] Filed: Jan. 13, 1993

[51] Int. Cl.$^5$ ............................................. A61C 1/05
[52] U.S. Cl. ................................... 433/132; 415/904
[58] Field of Search ........................ 433/132; 415/904

[56] References Cited

U.S. PATENT DOCUMENTS

| Re. 30,340 | 7/1980 | Borden | 433/132 |
|---|---|---|---|
| 3,120,705 | 2/1964 | Hoffmeister et al. | 433/132 |
| 3,298,103 | 1/1967 | Maurer | 433/132 |
| 3,306,375 | 2/1967 | Macks | 415/904 |
| 3,380,162 | 4/1968 | Heathe | 433/132 |
| 3,381,378 | 5/1968 | Lawrence | 415/904 |
| 3,408,043 | 10/1968 | Williams et al. | 433/132 |
| 3,418,715 | 12/1968 | Ellis | 433/132 |
| 4,146,964 | 4/1979 | Lares et al. | 433/132 |

FOREIGN PATENT DOCUMENTS

| 628810 | 10/1961 | Canada | 433/132 |
|---|---|---|---|
| 913106 | 12/1962 | United Kingdom | 433/132 |

Primary Examiner—Cary E. O'Connor
Attorney, Agent, or Firm—Frishauf, Holtz, Goodman & Woodward

[57] ABSTRACT

A high speed dental drill includes a drill head having a housing including a bottom and a cavity, and a turbine assembly mounted in the cavity for supporting a dental tool extending outwardly from the bottom of the housing, the turbine assembly including a rotor shaft and an annular turbine drive mounted thereon. The outer surface of the annular turbine drive has blades with an outer shape of a substantially inverted D-shaped chordal segment cut out therefrom so that rotation of the rotor shaft occurs at high speed when air impinges against the part-circular cut-away surfaces of the blades. Bearing assemblies rotatably support the shaft of the turbine assembly, and an exhaust is provided for exhausting air from the turbine assembly out of the bottom of the housing and to create and maintain positive air pressure in the housing, even during turn off of the drill, so as to prevent liquid from being drawn up into the housing, the exhaust including an exhaust hole in the bottom of the housing and an exhaust channel formed in the housing for supplying air to the exhaust hole from the turbine assembly. An elongated handle is connected with the housing, and has an air conduit in communication with the cavity of the housing for supplying pressure air against the turbine assembly, and a water conduit for supplying water under pressure through a water spray hole in the housing so that a water spray impinges upon the drilling tool during use.

40 Claims, 2 Drawing Sheets

HIGH SPEED DENTAL DRILL WITH POSITIVE PRESSURE AIR DRIVE

BACKGROUND OF THE INVENTION

This invention relates to a high speed dental drill, and more particularly to a high speed dental drill having contamination prevention means and an improved drive for high speed operations.

High speed, air-driven dental drills are known in the art, for example as disclosed in U.S. Pat. No. 4,203,221. With such dental drills, air enters the turbine area through an opening in the handpiece and passes over the rotatable vanes or blades that are secured to the outside of a rotor, thereby rotatably driving the drilling tool fixedly mounted to the rotor. However, such dental drills have relatively inefficient drive assemblies. As a result, it has been necessary to use a high velocity air stream to drive the rotor at high speeds. In practice, such drills rotate at speeds between about 320,000 rpm and about 500,000 rpm.

In order to avoid discomfort to the patient and so as not to interference with the drilling operation, it has been necessary to exhaust the high velocity air stream through an opening in the casing which does not face the patient, so that the exhausted air does not impinge on the patient. A typical construction for exhausting the spent drive air in a turbine-type high speed dental drill is shown as exhaust channel 75 in FIG. 5, which will be discussed further hereinbelow.

A recent problem, however, has arisen with respect to such high speed drills. Specifically, it has been found that, due to the high speed rotational nature of the drilling tool, there is a tendency for blood and other human fluids in the patient's mouth to be drawn up the drilling tool into the drill head. This primarily occurs at turn off of the compressed air drive source when the drill is to be turned off. At such time, suction forces are developed internally of the drill head due to inertia of the turbine member 134 which causes it to continue to rotate after turn off of the drive air. Accordingly, when the drill is used on the next patient, the blood or other human fluids from the prior patient's mouth, which had been drawn up into the drill head by such suction forces, can ride or flow down into the next patient's mouth. Thus, for example, if the first patient is HIV-positive, or carries other infectious diseases, the next patient can be contaminated with the HIV-positive (or otherwise contaminated) blood from the first patient.

Although this can be avoided by sterilizing the drill head after each use in an autoclave, the majority of dentists do not autoclave the drill head after each such use, but rather, at most, do so only at the end of each day or a few times during the day. Some practitioners also dip the drill in a disinfectant or wipe the drill head with disinfectant after each use. These precautions are not sufficient. Such superficial "cleaning" is usually done because if autoclaving is carried out after each use, the dentist would be required to purchase additional drills and drilling tools to use on the next patient while the autoclaving process is occurring with respect to the drill and drilling tool from the prior patient. This could increase the cost of the dental supplies to the dentist by many thousands of dollars. Moreover, autoclave sterilization between uses is only recommended, not required, by the American Dental Association. Accordingly, as described above, the majority of dentists merely wipe the outside of the drill head with a disinfectant between uses. This, however, does not eliminate the contaminated blood or other mouth fluids that have been drawn up inside the drill head.

It is an object of the present invention to provide an improved high speed dental drill in which positive air pressure is provided and maintained inside of the drill head so that the air used to power the turbine is positively exhausted, by the positive air pressure, toward the drilling tool so as to prevent contaminated blood from being drawn up into the drill head both during operation and during turning off of the drill.

A further object of the invention is to provide such an improved high speed dental drill in which the turbine can be driven with less air power so that the exhausted air is not uncomfortable to the patient and does not interfere with the drilling or other dental operation.

SUMMARY OF THE INVENTION

According to the present invention, a high speed dental drill includes a drill head having a housing including a bottom and a cavity therein. A turbine assembly is mounted in the cavity of the housing for supporting a dental tool extending outwardly from the housing, and a pair of bearing assembly (preferably comprising a pair of bearings) rotatably supports the turbine assembly in the cavity of the housing. An exhaust opening is provided for exhausting air from the turbine assembly out of the bottom of the housing so as to create a positive exhaust pressure at all times during use, even during turn off of the drill, to thereby prevent liquid from being drawn up into the housing of the dental drill during operation and during stopping of the drill. The high speed dental drill further includes an elongated handle having a distal end connected with the housing, the elongated handle including an air supply conduit in open communication with the cavity of the housing for supplying air under pressure to the turbine assembly to rotate the turbine assembly and thereby rotate the dental tool at high speed.

Specifically, the turbine assembly includes a rotor shaft rotatably supported by the bearing assemblies in the cavity of the housing, and an annular turbine drive mounted on the rotor shaft. The outer surface of the annular turbine drive has blades cut out therefrom, each of which has an outer shape of a substantially inverted D-shaped chordal segment. Thus, each turbine blade includes a part-circular edge having opposite ends connected by a straight connecting edge, and the outer surface of the turbine drive is cut-away therebetween such that an inclined part-circular cut-away surface is formed adjacent the part-circular edge. The air supply conduit of the elongated handle is arranged to supply air under pressure against the inclined part-circular cut-away surfaces. The handle does not have an elongated exhaust channel therein, which is provided in the prior art.

The elongated handle extends in a lengthwise direction, and the air supply conduit of the elongated handle supplies drive air under pressure against the turbine assembly at an angle to the lengthwise direction.

The exhaust includes an exhaust hole in the bottom of the housing and an exhaust channel formed in the housing for supplying air from the turbine assembly to the exhaust hole. Specifically, the bearing assemblies are fixedly supported by O-rings in the cavity of the housing, and the exhaust channel extends between the lower O-ring and the distal end of the elongated handle.

The elongated handle further includes a water spray hole adjacent the exhaust hole and a water conduit for supplying water under pressure through the water spray hole so that a water spray impinges upon the drilling tool.

DETAILED DESCRIPTION

Figure 1:
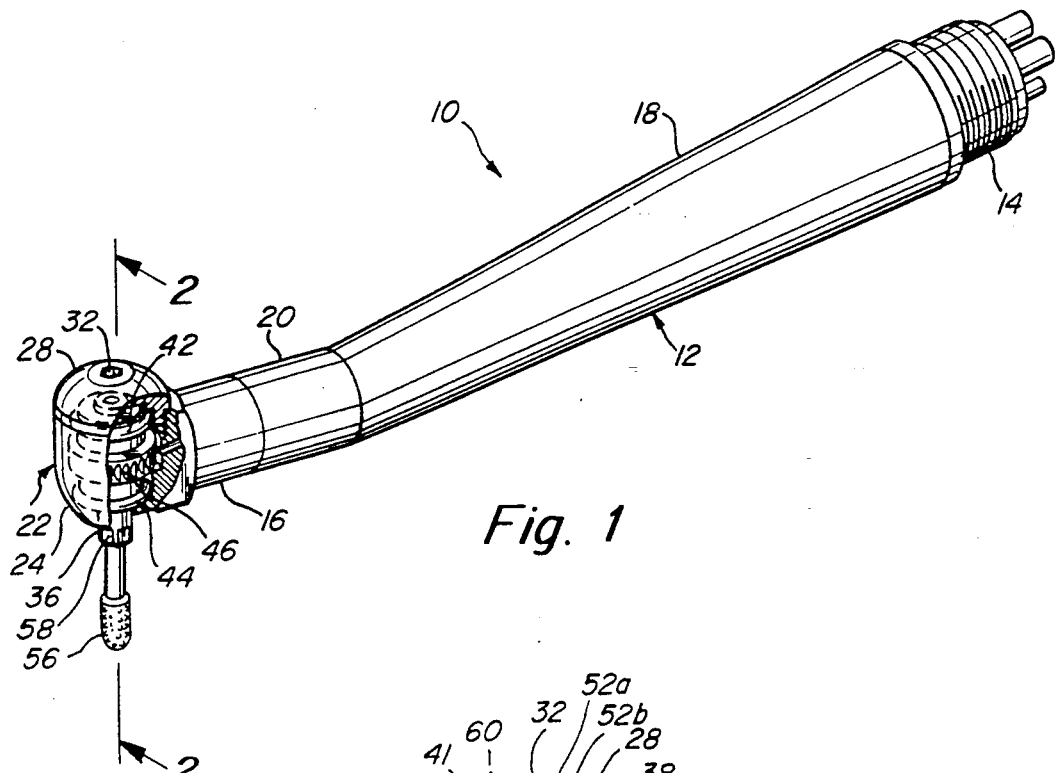
FIG. 1 is a perspective view of a high speed drill according to the present invention.

FIG. 1 shows a perspective view, partially cut-away and partially in phantom, of a high speed drill 10 of the present invention. The high speed drill comprises a handle 12 having a proximal end 14 and a distal end 16. Proximal end 14 is threaded for connection to a movable support (not shown), as is conventional. Connections other than threaded connections could be used, for example, a bayonet connection. Handle 12 includes an elongated barrel 18 extending from proximal end 14 and a neck 20 extending from distal end 16, with elongated barrel 18 and neck 20 being rigidly secured together at their opposite ends.

Figure 2:
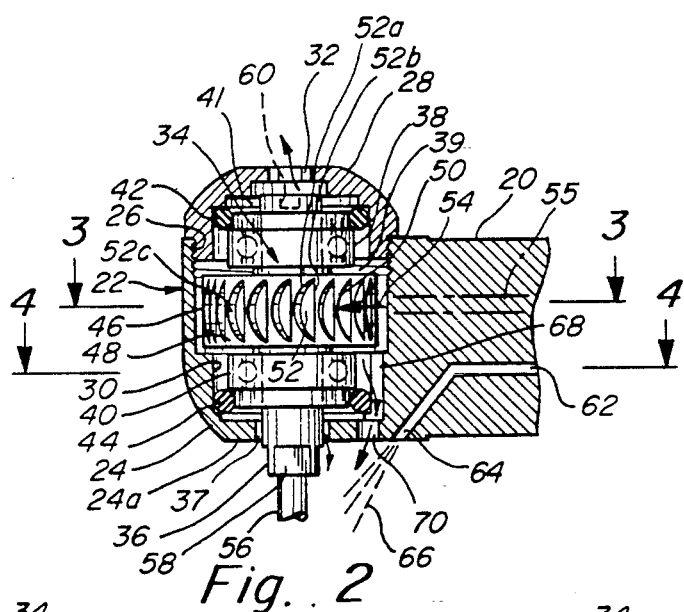
FIG. 2 is a section taken along line 2—2 of FIG. 1.

A drill head 22 is fixedly secured at distal end 16, that is, to the distal end of neck 20. Specifically, as best seen in FIGS. 1 and 2, drill head 22 includes a cup-shaped main housing 24 that is fixed to the distal end of neck 20. Main housing 24 has a threaded, upper open end 26, and a head cover 28 is threadedly secured thereto in covering relation, whereby an internal cavity 30 is formed therein. To threadedly secure and/or remove head cover 28, a hexagonal opening 32 is formed centrally of head cover 28 for receiving a conventional Allen wrench tool.

A turbine assembly 34 is rotatably mounted in cavity 30. Specifically, turbine assembly 34 includes a rotor shaft 36 rotatably journalled between an upper ball bearing assembly 38 and a lower ball bearing assembly 40. Ball bearing assemblies 38 and 40 are non-rotatably held in position by means of upper and lower O-rings 42 and 44, respectively, which also function to provide a seal for the cavity. Accordingly, with ball bearing assemblies 38 and 40 held in place, rotor shaft 36 is free to rotate.

Figure 5:
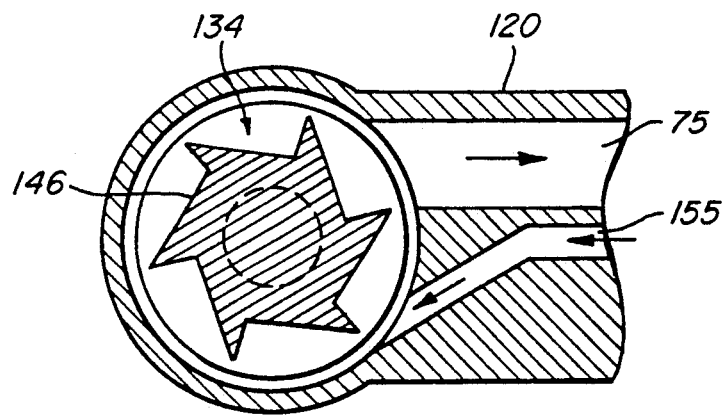
FIG. 5 shows a prior art turbine and air exhaust arrangement.

An annular turbine drive 46 is mounted substantially centrally on rotor shaft 36 and has an annular outer surface 48 with a plurality of blades 50 spaced therearound and which are cut out from outer surface 48, each blade having a general outer shape of a substantially inverted D-shaped chordal segment of a circle. Thus, each blade 50 includes a part-circular edge 52a having opposite ends connected by a straight connecting edge 52b, and outer surface 48 is cutaway therebetween such that an inclined part-circular cutaway surface 52c and an opposite backward-facing surface 52 formed adjacent part-circular edge 52a. Thus, as air impinges against outer surface 48, and particularly, against inclined part-circular cut-away surfaces 52c of blades 50, as shown by arrow 54 in FIG. 2, turbine drive 46 and rotor shaft 36 are caused to rotate. The shape of blades 50 is important to provide an efficient rotation with a lower velocity air stream than necessary according to known high speed drills. The large number of blades 50 is also very important to the present invention. Preferably, 10-35 blades are provided, wherein the prior art generally provides 6-8 blades, as seen in FIG. 5. The shown embodiment of the invention uses 24 of the blades 50 and it has been found that 16 blades also provides good performance.

In order to impinge such drive air onto turbine drive 46, a continuous input air conduit 55 extends through barrel 18, neck 20 and main housing 24, and exits through an air outlet port 57 at the inner surface of main housing 24. As shown best in FIG. 3, input air conduit 55 extends along the axis of barrel 18, and is then bent at an oblique angle of approximately 160°-165° in neck 20 and main housing 24 so as to impinge at an angle upon inclined part-circular cut-away surfaces 52c of turbine blades 50. The input air conduit 55 could be bent at angles other than 160°-165°, as described. With this arrangement, a low volume of input drive air can be used for rotating turbine drive member 46 at a high speed and with a high torque.

The structure of the present invention is able to achieve high rotational speeds (for example from about 320,000 rpm to about 500,000 rpm) while also providing extremely high torque (higher than is available in many existing devices). By eliminating the prior art exhaust channel 75 in the body of the housing 120 (see FIG. 5), a pressure differential which would normally exist on the rotating vanes of the turbine drive member 146 during turn off of the drill, and which would create a suction or sucking-in force, is eliminated. In the prior art device shown in FIG. 5, if the exhaust 75 is provided, the pressure surrounding the outer periphery of the turbine drive member 46, and acting on the rotating vanes thereof, during turn off of the drill, is gradually reduced from the point at which the high pressure is introduced at conduit 155 to the point at which the exhaust air is exhausted at the outlet of channel 75. During turn off, the supply of air through air supply channel 155 is sharply turned off. The continued rotation of rotor 134 due to inertia therefore creates a suction in the drill head and mouth fluids are sucked in via the various clearances near the drill bit, etc. In the present invention, as seen for example in FIG. 3, the air pressure surrounding the outer periphery of the vanes 50, and which exists in the space 51 between the outer periphery of the vanes 50 and the inner wall of the housing portion 24, is substantially constant around the complete periphery of the turbine drive member 46 (since no exhaust channel 75 exists), thus preventing exerting a drag on the rotating member 46 due to decreasing air pressure at various points around the rotating member 46. Since, in the present invention, the air pressure surrounding member 46 is substantially constant throughout, drag forces (and pressure differentials) are not applied thereto and more efficient rotation of the turbine is achieved. Also, the undesired suction forces of the prior art are eliminated at turn off, and positive pressure is maintained inside the drill head at all times, even during turn off. Thus, high rotational speeds with low input pressure and with high torque are achieved in a simple and efficient manner, while also positively preventing contamination of the interior of the drill tool.

Figure 3:
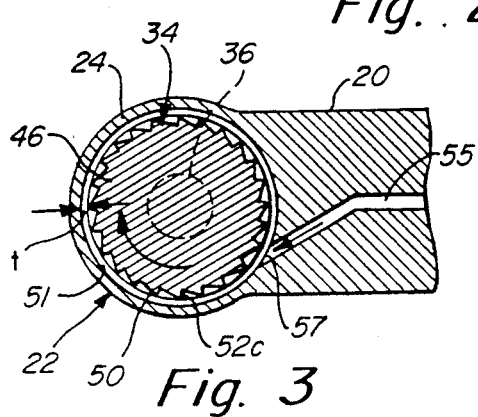
FIG. 3 is a section taken along line 3—3 of FIG. 2.
Figure 4:
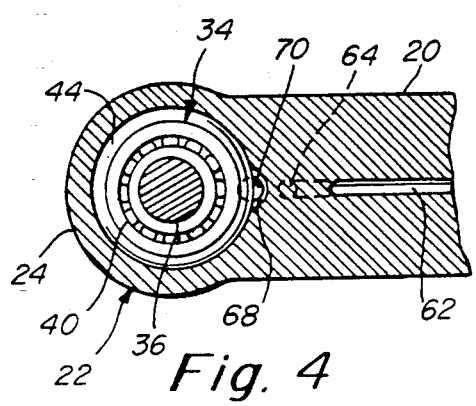
FIG. 4 is a section taken along line 4—4 of FIG. 2.

The clearance "t" shown in FIG. 3 may be from about 0.05 mm to about 0.5 mm, and is preferably about 0.1 mm to 0.3 mm.

Thus, with above arrangement, because of the particular formation and arrangement of turbine blades 50, and the construction which eliminates the exhaust channel 75 of the prior art (see FIG. 5), and because of the positive exhaust clearances of the present invention, a low volume of air can be used to obtain high speed rotation of the drilling tool 56. Since only a low volume of drive air is required, the exhaust air is also of low volume and relatively low pressure and can thus be safely exhausted even in the direction of the patent's mouth, without damaging tissue of the patient and without discomfort to the patient.

According to the technique of the present invention, input air is exhausted from the turbine drive through the clearance "t" shown in FIGS. 2 and 3 (wherein the air is at approximately a substantially equal pressure around the entire periphery of turbine drive 46), downward through exhaust channel 68 and out through exhaust opening 70, through the bearings 40 and out through the clearance 37 between the rotor shaft 36 and the housing 24 (as shown by arrows), and upwardly out through the space 39, through the clearances of the upper ball bearing assembly 38, through the space 41 and out through hole 60 of the head cover 28, as indicated by the upwardly directed arrow in FIG. 2. As a result, exhaust air, which provides the positive air pressure within the housing 24 to prevent internal contamination thereof, is fed mainly out of the bottom portion of the housing 22, but a substantial amount of air is also fed positively outwardly through the upper portion of the housing 22 (through opening 32) to prevent contamination from entering through the upper portion of the tool. The clearances in the respective bearing assemblies, and the various clearances which are specifically provided in the apparatus of the present invention and the various exhaust openings, all cooperate to provide a positive pressure within the housing of the dental tool 24 to prevent internal contamination thereof during use, provide very little back pressure on the rotor assembly 46, and provide a very simple and easy to manufacture structure which provides the desirable characteristics of very high rotational speeds with very little back pressure applied to the rotor 46, a high torque, positive output of air and liquid to cool and lubricate the working surface, and to also prevent contamination from entering the internal portions of the high speed drill assembly.

Figure 6:
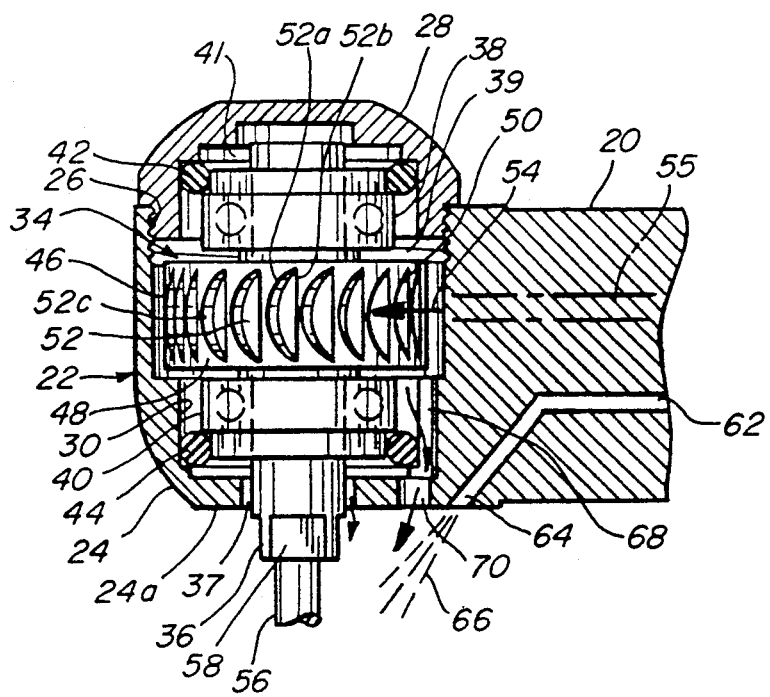
FIG. 6 shows another embodiment of the present invention with a closed top member.

As shown in FIGS. 1 and 2, a drilling tool 56 is removably fixed through the lower end of rotor shaft 36. Such attachment is accomplished in a conventional manner. For example, rotor shaft 36 can have an internal chuck (not shown) which can be opened and closed by turning the upper end of rotor shaft 36 relative to the lower end thereof. For example, the lower end of rotor shaft 36 can have four flat sections 58 therearound for preventing rotation of rotor shaft 36, while a square hole 60 is provided at the upper end thereof. A wrench (not shown) can be inserted through hexagonal opening 32 for insertion within square hole 60 so as to turn the upper end of rotor shaft 36 relative to the lower end thereof, and thereby change drilling tools. FIG. 6 shows an embodiment without opening 32 or square hole 60, wherein a self-locking chuck or the like is used. In the case of FIG. 6, all of the exhaust air exits via the bottom portion.

In addition, as is conventional, a water conduit 62 extends through barrel 18 and neck 20, and is bent so as to exit through a water spray hole 64 at the bottom of neck 20. Accordingly, a water spray 66 is projected toward the lower end of drilling tool 56.

In accordance with another important aspect of the present invention, because the air used to drive turbine assembly 34 is of a low volume, such air can be exhausted in the direction of the patient, in combination with coolant spray 66, that is, from the bottom of drill head 22, without any discomfort to the patient and so as not to interfere with the drilling operation. Thus, less air can be used in the liquid (water) spray line 62, and better directionality of the spray 66 is achieved. In this regard, an exhaust channel 68 is formed in main housing 24 between lower O-ring 44 and neck 20. Exhaust channel 68 is in communication with an exhaust hole 70 in the bottom 24a of main housing 24, adjacent the lower end of rotor shaft 36. The air exhausted form exhaust hole 70 cooperates with the spray 66 from spray hole 64 to make the spray 66 more parallel to the working tool 56, thus improving cooling and lubrication of the working surfaces of tool 56 during operation.

Thus, the air exhausted from air exhaust hole 70 and the spray 66 are caused to impinge on an upper or middle portion of drilling tool 56, and to flow toward the working tip of the tool 56, thereby positively preventing any blood or other mouth liquids from the patient from being drawn up into drill head 22. Positive air pressure is also built up inside the drill head 22, as discussed above, to prevent contamination of the internal portions thereof, during operation as well as during turn off. Thus, dual prevention of drill head contamination is achieved.

As discussed above, because of the use of low velocity air to drive turbine assembly 34, such air can be safely exhausted toward the patient so as to prevent any contamination of drill head 22 by liquids being drawn up drilling tool 56. In other words, a high positive air pressure is maintained on drilling tool 56 and in the inside of drill head 22 to prevent contaminated liquids from being drawn up into drill head 22.

Also, a smaller diameter inlet channel 55 can be used in the present invention. Typical prior art air inlet channels 155 (FIG. 5) are at least about 1.2 mm in diameter. In the present invention, good performance is achieved even when using air inlet channels of about 1 mm or less.

Having described a specific preferred embodiment of the invention with reference to the accompanying drawings, it will be apparent that the present invention is not limited to that specific embodiment, and that various changes and modifications can be made by one of ordinary skill in the art, and the various features can be used in any combination, without departing from the scope or spirit of the invention as defined in the appended claims.

What is claimed is:
1. A high speed dental drill comprising:
 a drill head including:
  a housing including a bottom and a top, and a cavity therein;
  turbine assembly means mounted in said cavity of said housing for supporting a dental tool extending outwardly from said housing;
  support means for rotatably supporting said turbine assembly means in said cavity of said housing;
  an elongated handle having a distal end connected with said housing, said elongated handle including air conduit means in open communication with said cavity of said housing for supplying driving air under pressure against said turbine assembly means so as to cause rotation of said turbine assembly means and rotation of said tool, the air being exhausted from said turbine assembly means after the air is passed through said turbine assembly means to cause said rotation; and exhaust means for exhausting substantially all of said exhaust air from said turbine assembly means out of said bottom of said housing so as to create and maintain a positive air pressure in said housing at all times, even during turn off of the drill, so as to prevent liquid from a patient's mouth from being drawn by suction into said cavity of said housing.

2. A high speed dental drill according to claim 1, wherein said exhaust means further includes means for exhausting a minor amount of exhaust air from said turbine assembly means out of said top of said housing.

3. A high speed dental drill according to claim 2, wherein said top of said housing includes an opening for insertion of an operating tool, said exhaust means including means for directing said minor amount of exhaust air from said turbine assembly means through internal portions of said housing and out of said opening in said top of said housing.

4. A high speed dental drill according to claim 2, wherein said support means includes bearings for rotatably supporting said turbine assembly means in said cavity of said housing, said bearings have clearances for air passage therethrough, and wherein at least said exhaust means includes means for exhausting said minor amount of said exhaust air from said turbine assembly means through said clearances of said bearings and out of said bottom and top of said housing.

5. A high speed dental drill according to claim 2 wherein said support means includes bearings for rotatably supporting said turbine assembly means in said cavity of said housing, said bearings have clearances for air passage therethrough, and wherein said exhaust means includes means for exhausting air from said turbine assembly means through said clearances of said bearings and out of said bottom and top of said housing.

6. A high speed dental drill according to claim 5, wherein said turbine assembly means includes between ten and thirty-five blades thereon.

7. A high speed dental drill according to claim 6, wherein a clearance is provided between the outermost surfaces of said blades and an inner surface of said cavity of said housing adjacent said outermost surfaces of said blades, said clearance being between about 0.05 mm and about 0.5 mm.

8. A high speed dental drill according to claim 7, wherein said clearance is between about 0.1 mm and about 0.3 mm.

9. A high speed dental drill according to claim 1, wherein said exhaust means includes an exhaust hole in said bottom of said housing, and exhaust channel means formed in said housing for supplying air exhausted from said turbine assembly means to said exhaust hole.

10. A high speed dental drill according to claim 9, wherein said support means includes bearing means for rotatably supporting said turbine assembly means and O-ring means, for fixedly supporting said bearing means in said cavity of said housing, and said exhaust channel means extends between said O-ring means and said distal end of said elongated handle.

11. A high speed dental drill according to claim 9, wherein said dental tool extends outwardly from said housing from said bottom of said housing and adjacent to said exhaust hole.

12. A high speed dental drill according to claim 11, wherein said support means includes bearing means for rotatably supporting said turbine assembly means and O-ring means for fixedly supporting said bearing means in said cavity of said housing, and said exhaust channel means extends between said O-ring means and said distal end of said elongated handle.

13. A high speed dental drill according to claim 9, wherein said drill head further includes a water spray hole adjacent said exhaust hole, and said elongated handle includes water conduit means for supplying water under pressure through said water spray hole so that a water spray impinges upon said drilling tool during use.

14. A high speed dental drill according to claim 1, wherein said turbine assembly means includes an outer surface having blades cut out from said outer surface, said blades having an outer configuration substantially in the shape of a chordal segment of a circle.

15. A high speed dental drill according to claim 14, wherein said turbine assembly means includes a rotor shaft rotatably supported by said support means in said cavity of said housing, and an annular turbine drive mounted on said rotor shaft, said annular turbine drive including said outer surface.

16. A high speed dental drill according to claim 15, wherein each blade of said turbine includes a part-circular edge having opposite ends connected by a straight connecting edge, with said outer surface being cut-away therebetween, such that an inclined part-circular cut-away surface is formed adjacent said part-circular edge.

17. A high speed dental drill according to claim 16 wherein said air conduit means of said elongated handle is arranged to supply air under pressure against said inclined part-circular cut-away surfaces.

18. A high speed dental drill according to claim 1, wherein said elongated handle extends in a lengthwise direction, and said air conduit means of said elongated handle supplies said air under pressure against said turbine assembly means at an angle to said lengthwise direction.

19. A high speed dental drill according to claim 1, wherein said dental tool extends outwardly from said housing through said bottom of said housing.

20. A high speed dental drill according to claim 19, wherein said exhaust means comprises an opening in said bottom of said housing for exhausting said air from said turbine assembly means, said opening being adjacent to said dental tool which extends outwardly from said bottom of said housing, and said opening directing said exhaust air to impinge upon said dental tool during use.

21. A high speed dental drill according to claim 20, wherein said drill head further includes a water spray hole adjacent said exhaust hole, and said elongated handle includes water conduit means for supplying water under pressure through said water spray hole so that a water spray impinges upon said dental tool during use.

22. A high speed dental drill comprising:
a drill head including:
a housing including a bottom and a top, and a cavity therein;

turbine assembly means mounted in said cavity of said housing for supporting a dental tool extending outwardly from said housing;

support means for rotatably supporting said turbine assembly means in said cavity of said housing;

an elongated handle having a distal end connected with said housing, said elongated handle including air conduit means in open communication with said cavity of said housing for supplying driving air under pressure against said turbine assembly means so as to cause rotation of said turbine assembly means and rotation of said tool, the air being exhausted from said turbine assembly means after the air is passed through said turbine assembly means to cause said rotation; and exhaust means for exhausting at least 60% of said exhaust air from said turbine assembly means out of said bottom of said housing and for exhausting the remainder of said exhaust air from said turbine assembly means out of said top of said housing, so as to create and maintain a positive air pressure in said housing at all times, even during turn off of the drill, so as to prevent liquid from a patient's mouth from being drawn by suction into said cavity of said housing.

23. A high speed dental drill according to claim 22, wherein said top of said housing includes an opening for insertion of an operating tool, said exhaust means including means for directing said remainder of said exhaust air from said turbine assembly means through internal portions of said housing and out of said opening in said top of said housing.

24. A high speed dental drill according to claim 22, wherein said support means includes bearing for rotatably supporting said turbine assembly means in said cavity of said housing, said bearings have clearances for air passage therethrough, and wherein said exhaust means includes means for exhausting at least said remainder of said exhaust air from said turbine assembly means through said clearances of said bearings and out of said bottom and top of said housing.

25. A high speed dental drill according to claim 22, wherein said exhaust means includes an exhaust hole in said bottom of said housing and exhaust channel means formed in said housing for supplying air exhausted from said turbine assembly means to said exhaust hole.

26. A high speed dental drill according to claim 25, wherein said support means includes bearing means for rotatably supporting said turbine assembly means, and O-ring means for fixedly supporting said bearing means in said cavity of said housing, and said exhaust channel means extends between said O-ring means and said distal end of said elongated handle.

27. A high speed dental drill according to claim 25, wherein said dental tool extends outwardly from said housing from said bottom of said housing and adjacent to said exhaust hole.

28. A high speed dental drill according to claim 27, wherein said support means includes bearing means for rotatably supporting said turbine assembly means, and O-ring means for fixedly supporting said bearing means in said cavity of said housing, and said exhaust channel means extends between said O-ring means and said distal end of said elongated handle.

29. A high speed dental drill according to claim 22, wherein said support means includes bearings for rotatably supporting said turbine assembly means in said cavity of said housing, said bearings have clearances for air passage therethrough, and wherein said exhaust means includes means for exhausting air from said turbine assembly means through said clearances of said bearings and out of said bottom and top of said housing.

30. A high speed dental drill according to claim 22, wherein said turbine assembly means includes an outer surface having blades cut out from said outer surface, said blades having an outer configuration substantially in the shape of a chordal segment of a circle.

31. A high speed dental drill according to claim 22, wherein said turbine assembly means includes between ten and thirty-five blades thereon.

32. A high speed dental drill according to claim 31, wherein a clearance is provided between the outermost surfaces of said blades and an inner surface of said cavity of said housing adjacent said outermost surfaces of said blades, said clearance being between about 0.05 mm to about 0.5 mm.

33. A high speed dental drill according to claim 32, wherein said clearance is between about 0.1 mm and about 0.3 mm.

34. A high speed dental drill comprising:
a drill head including:
a housing including a bottom and a top, and a cavity therein;
turbine assembly means mounted in said cavity of said housing for supporting a dental tool extending outwardly from said housing;
support means for rotatably supporting said turbine assembly means in said cavity of said housing;
an elongated handle having a distal end connected with said housing, said elongated handle including air conduit means in open communication with said cavity of said housing for supplying driving air under pressure against said turbine assembly means so as to cause rotation of said turbine assembly means and rotation of said tool; and
exhaust means for exhausting air from said turbine assembly means out of said bottom of said housing so as to create and maintain a positive air pressure in said housing at all times, even during turn off of the drill, so as to prevent liquid from a patient's mouth from being drawn by suction into said cavity of said housing;
said exhaust means including an exhaust hole in said bottom of said housing, and exhaust channel means in said housing for supplying air exhausted from said turbine assembly means to said exhaust hole; and
wherein said support means includes bearing means for rotatably supporting said turbine assembly means, and O-ring means for fixedly supporting said bearing means in said cavity of said housing, and wherein said exhaust channel means extends between said O-ring means and said distal end of said elongated handle.

35. A high speed dental drill according to claim 34, wherein said dental tool extends outwardly from said housing from said bottom of said housing and adjacent to said exhaust hole.

36. A high speed dental drill according to claim 34, wherein said bearings have clearances for air passage therethrough, at least some of said exhaust air being exhausted through said clearances of said bearings.

37. A high speed dental drill according to claim 34, wherein said turbine assembly means includes an outer surface having blades cut out from said outer surface, said blades having an outer configuration substantially in the shape of a chordal segment of a circle.

38. A high speed dental drill according to claim 34, wherein said turbine assembly means includes between ten and thirty-five blades thereon.

39. A high speed dental drill according to claim 38, wherein a clearance is provided between the outermost surfaces of said blades and an inner surface of said cavity of said housing adjacent said outermost surfaces of said blades, said clearance being between about 0.05 mm and about 0.5 mm.

40. A high speed dental drill according to claim 39, wherein said clearance is between about 0.1 mm and about 0.3 mm.

* * * * *